United States Patent
Pennig

Patent Number: 5,709,687
Date of Patent: Jan. 20, 1998

[54] FIXATION PIN FOR SMALL-BONE FRAGMENTS

[76] Inventor: Dietmar Pennig, Hans-Driesch-Strasse 12, 50935, Köln, Germany

[21] Appl. No.: 679,626

[22] Filed: Jul. 12, 1996

Related U.S. Application Data

[63] Continuation-in-part of Ser. No. 392,386, Feb. 22, 1995, Pat. No. 5,609,595, said Ser. No. 392,386, is a continuation-in-part of Ser. No. 214,365, Mar. 16, 1994, Pat. No. 5,433,719.

[51] Int. Cl.$^6$ .................................................. A61B 17/58
[52] U.S. Cl. ........................ 606/73; 606/72; 606/69; 606/65; 411/368; 411/401; 411/424
[58] Field of Search ................................ 606/60, 65, 72, 606/73, 69, 104; 411/401, 411, 413, 424, 426, 368, 366, 371, 155, 156, 544, 442

[56] References Cited

U.S. PATENT DOCUMENTS

| | | | |
|---|---|---|---|
| 4,524,765 | 6/1985 | De Zbikowski | 606/73 |
| 4,963,144 | 10/1990 | Huene | 606/72 |
| 5,196,016 | 3/1993 | Buser et al. | 606/73 |
| 5,368,593 | 11/1994 | Stark | 606/72 |
| 5,511,301 | 4/1996 | McGuire | 411/368 |

*Primary Examiner*—Michael Buiz
*Assistant Examiner*—Daphna Shai
*Attorney, Agent, or Firm*—Hopgood, Calimafde, Kalil & Judlowe

[57] ABSTRACT

The invention contemplates a compression wire for fixated retention of a fractured small bone fragment in an osteosynthesis procedure. The wire comprises a smooth-walled shank portion and an adjoining threaded portion, of lesser diameter than the diameter of the shank portion, there being a step-down shoulder between the shank portion and the threaded portion. The shank portion is adapted for chucked engagement to a portable rotary drill, and the distal end of the threaded portion is configured for self-tapping entry into and threaded implantation in bone. The implantation is complete when the shoulder engages cortex tissue of the fragment, holding the same in compression against remainder structure of the fractured bone. Once implanted, the shank may be nipped by a cutter tool at relatively close offset from the shoulder.

35 Claims, 4 Drawing Sheets

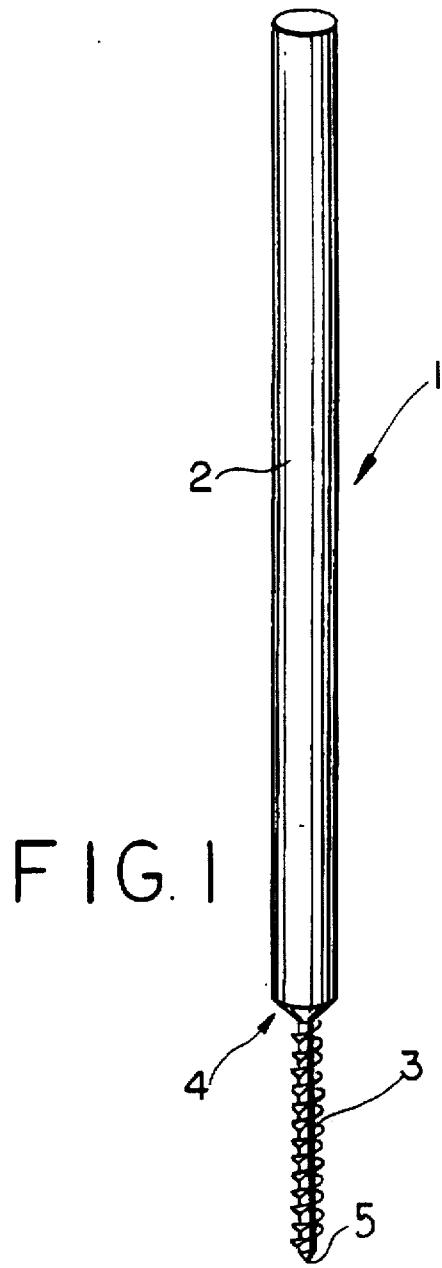
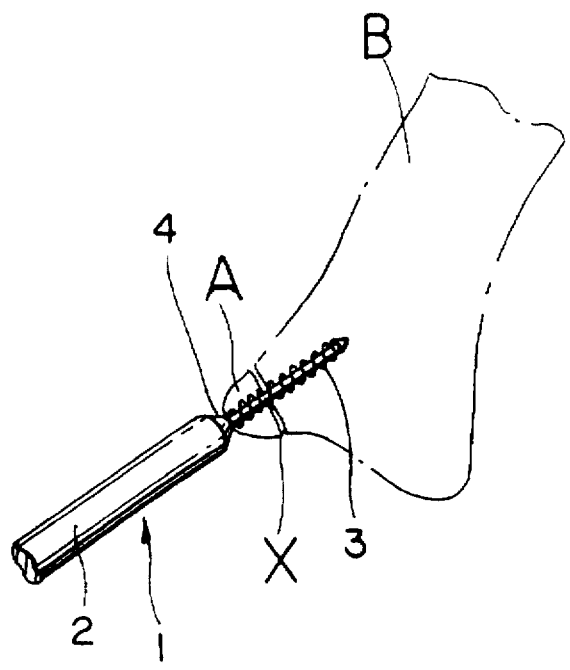

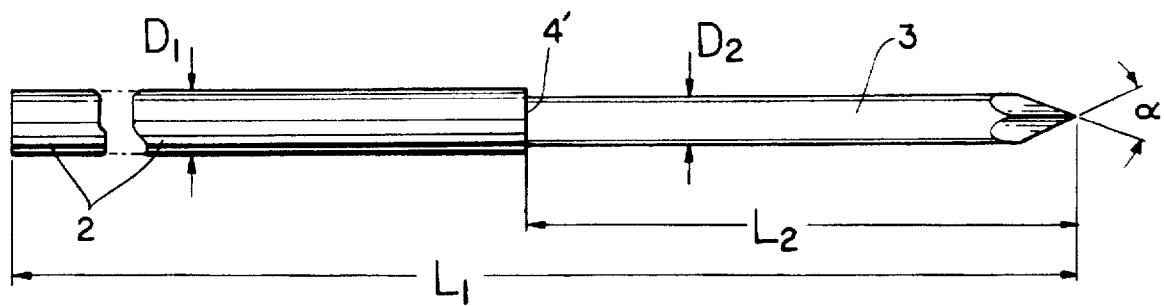
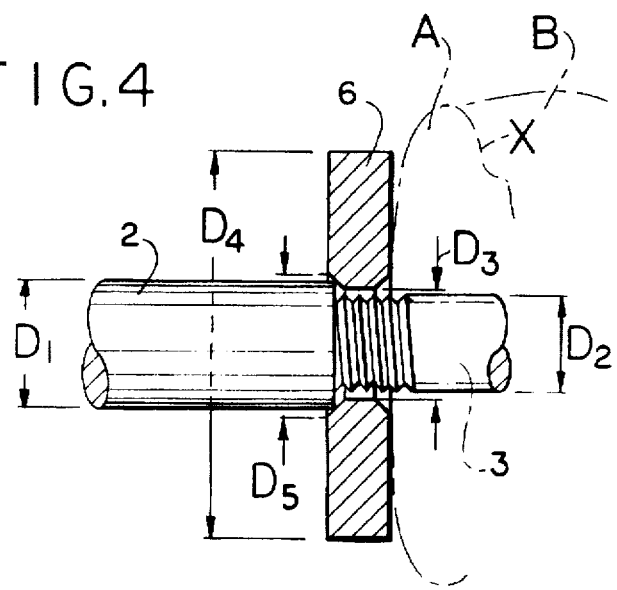 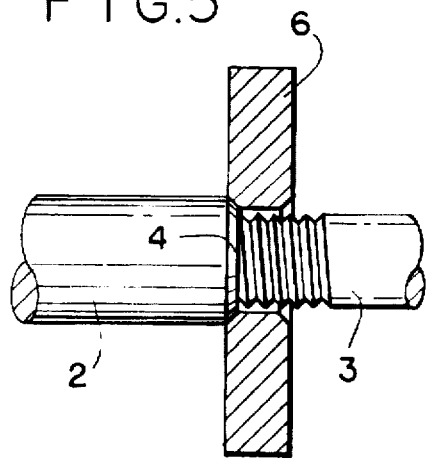
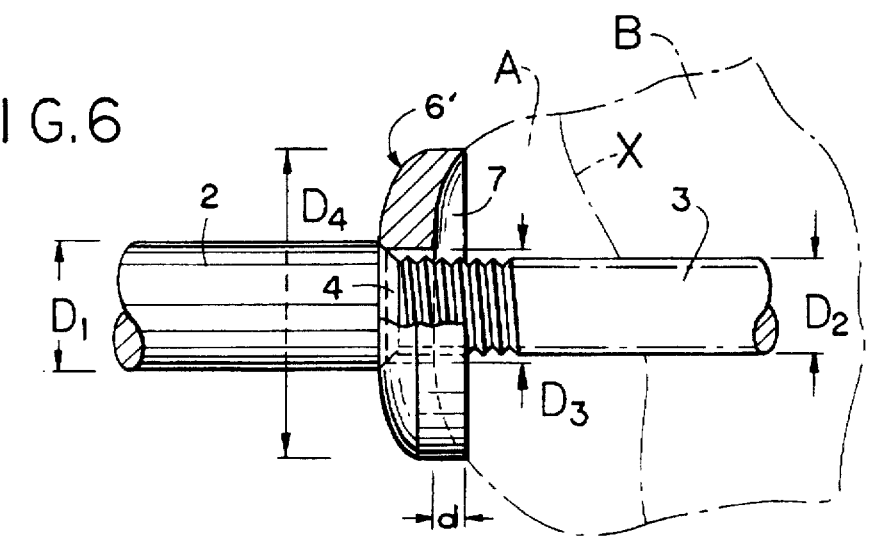

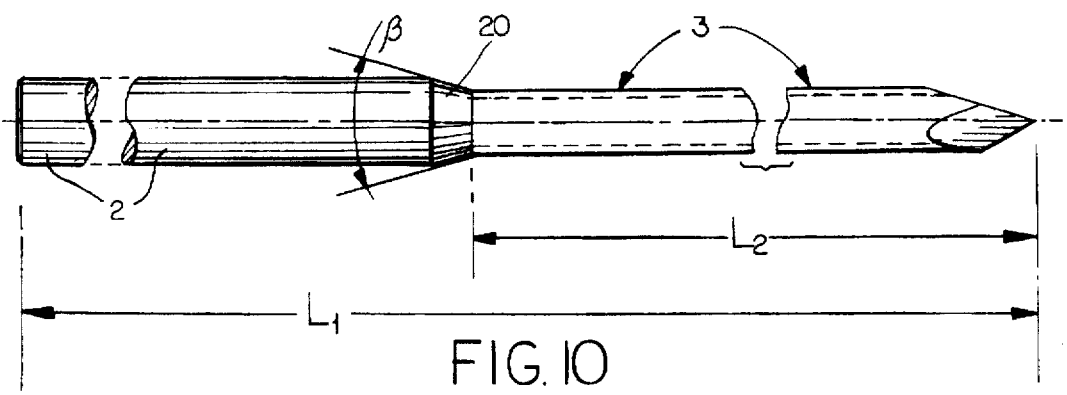
FIG. 10
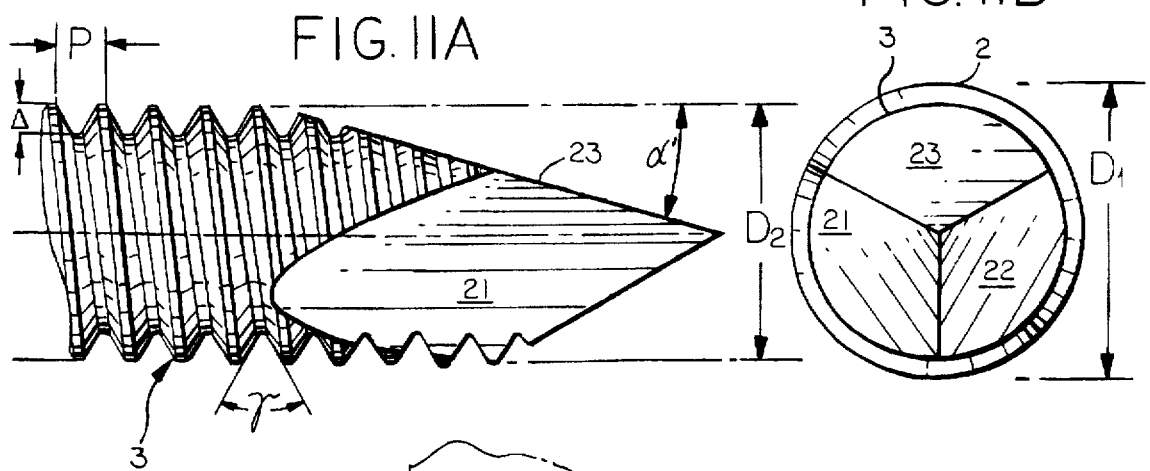
FIG. 11A
FIG. 11B
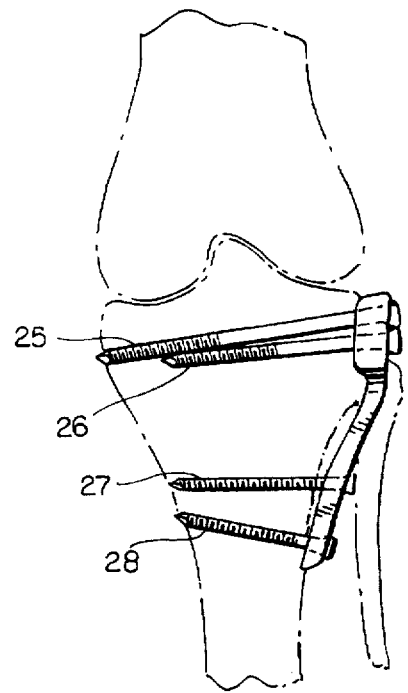
FIG. 12

FIXATION PIN FOR SMALL-BONE FRAGMENTS

RELATED CASE

This application is a continuation-in-part of application, Ser. No. 08/392,386, filed Feb. 22, 1995 now U.S. Pat. No. 5,609,595, and said Ser. No. 08/392,386 is a continuation-in-part of original application Ser. No. 08/214,365, filed Mar. 16, 1994 (now U.S. Pat. No. 5,433,719).

BACKGROUND OF THE INVENTION

The present invention relates to a fixation pin for use in retaining small-bone fragments in an osteosynthesis procedure.

It is generally known in osteosyntheses to fix bone fragments by screws or pins. In the case of small-bone splinterings, the screws or pins available in the prior art are, however, much too large to fix a small splintered portion of a given bone to another portion of the same bone without damaging these parts. The fixing of such small bone fragments by means of simple pins or nails is therefore problematical, since there is no abutment to hold the parts together, and the bone may shift on the outer wall of the pin or nail.

More specifically, the use of Kirschner wires (K-wires) in small-bone and bone-fragment fixation dates back to the early part of this century and is a common procedure in orthopedics, offering advantages of simplicity of use, and low cost. Threaded K-wires, designed to produce better anchorage in bone, were a later modification. And small-fragment screws, using the lag-screw principle were in wide use in the 1970's, to provide rigid fixation of small fragments. However, all of these techniques had their disadvantages.

K-wires offer poor purchase; a fragment can slide with respect to a wire. Any bending of a wire, as for securing purposes, may result in displacement or fracture of a fragment. And wire migration into a joint through the skin carries the risk of infection.

Threaded K-wires have only a small distal threaded portion, which can improve anchorage to the main or larger bone fragment to which a smaller fragment is to be reunited; but most of the disadvantages of the K-wire remain.

Use of the lag-screw technique involves a more complex procedure; two drill sizes are required for pre-drilling, and there must be a pretapping of bone. This technique is not suitable for small bone fragments, and there is risk of bone contamination.

BRIEF STATEMENT OF THE INVENTION

The object of the present invention is to provide a fixation pin for bone fragments which, despite its necessarily small size, will produce a dependable fixation of a small-bone fragment to the adjacent remainder of the bone from which the fragment developed.

Another object is to achieve the above object in a single motor-driven operation which assures prolonged retention of the fixation.

It is a specific object to meet the above objects, even for the case of a bone fragment that must be restored to its former location as part of the cancellous structure, as at an end of a long bone.

The invention achieves these objects by providing a small-bone pin or wire with an elongate smooth-walled shank. The distal end portion of the pin has a step-down transition to a smaller-diameter threaded portion, with a sharp distal point for self-tapping entry into bone. The step-down transition provides a shoulder which may be radial but is preferably conical and which can abut a bone fragment or splinter, while the threaded portion is anchored to the main part of the same bone.

Stated in other words, a small-bone pin of the invention has a smooth-walled shank portion along a relatively large part of the overall length of the pin, and a relatively short threaded part with a sharp bone-cutting distal tip extends beyond the shank portion; the threaded portion is advantageously developed with fine threads, i.e., of relatively small thread advance per turn so that a smooth and precise feeding implantation of the pin is possible. In use of this pin, the shank is chucked to a portable drill, and the threaded portion is driven into the bone fragment and into the remainder or main fraction of the same bone; exposed cortex of the bone fragment is abutted by the shoulder or conical step formed between the threaded portion and the shank portion, so that the fragment is fixed to the remainder of the original bone with a degree of compression best judged by the surgeon, and it is no longer possible for the bone fragment to slide on the pin.

When relying solely upon the small-bone pin of the invention, the shank portion may be located within surrounding muscular tissue. The shank portion also projects externally, for easy chuck access and for later cut-off to desired length, using a suitable tool; in that event, it is appropriate to refer to the bone pin of the invention as a compression wire. The expression "compression wire" is therefore in frequent use in this specification.

Optionally, and depending upon the shape or condition of the proximal face of the bone fragment to be secured, a special washer is applicable over the threaded portion of the pin (a) with a counterbore adapted to locate against the shoulder, (b) with a larger diameter than that of the shank portion of the pin, and (c) with a distal face adapted for relatively large-area retaining engagement with the bone fragment.

DETAILED DESCRIPTION OF THE DRAWINGS

Preferred embodiments of the invention will be described in conjunction with the accompanying drawings, in which:

FIG. 1 is an enlarged view in elevation of a small-bone pin or compression wire of the invention;

FIG. 2 is a simplified section, on a reduced scale, through a small bone, fractured at X, to show use of the invention;

FIG. 3 is a view in longitudinal elevation of a modified small-bone pin or compression wire;

FIG. 4 is an enlarged fragmentary view of coacting elements of the invention in an installed condition, pursuant to an optional employment of kit components of the invention;

FIG. 5 is a view similar to FIG. 4, for a further modification;

FIG. 6 is another enlarged fragmentary view of coacting elements of the invention in an installed condition, pursuant to a further optional employment of kit components of the invention;

FIG. 10 is a longitudinal elevation of a compression wire of the invention, to show a presently preferred modification;

FIG. 11A is a greatly enlarged fragmentary view of the distal-tip end of the modification of FIG. 10;

FIG. 11B is a right-end view of structure of FIG. 11A; and

FIG. 12 is a diagram, simplified from an x-ray photograph to show use of multiple compression wires of the invention to serve tasks other than bone-fragment fixation.

DETAILED DESCRIPTION

Figure 7A:
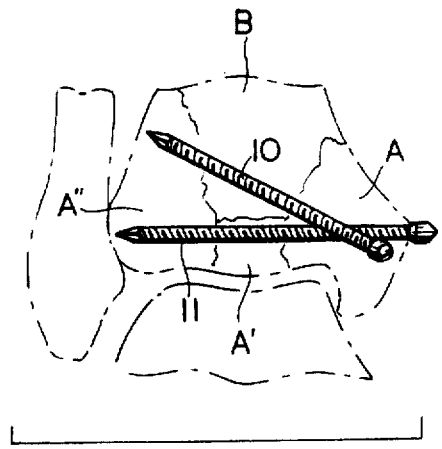
FIG. 7A is a diagram in the nature of FIG. 2, and simplified from an x-ray photograph, to show use of multiple implanted compression wires of relatively large diameter, in the fixation of a comminuted pilon tibial fracture.
Figure 7B:
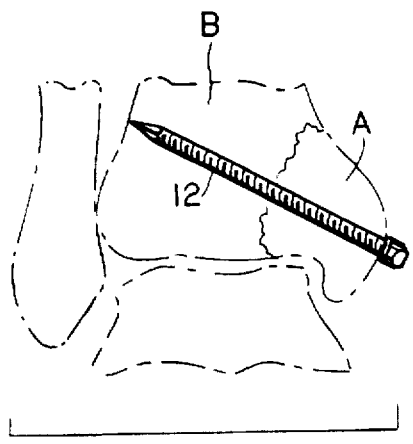
FIG. 7B is a simplified diagram as in FIG. 7A to show the same compression-wire size in the fixation of a medial malleolar fracture.

In FIG. 1, a small-bone fixation pin or compression wire 1 is seen to comprise essentially a smooth-walled shank portion 2, with an adjoining distal threaded portion 3. The outside diameter of the threaded portion 3 is smaller than the outside diameter of the shank portion 2; the diameter of the threaded portion is preferably constant, except for a sharp distal end 5, for self-threading and self-tapping entry into bone tissue. Between the threaded portion 3 and the shank portion 2, as seen in FIG. 2, a frusto-conical shoulder or step 2 serves as an abutment for a bone fragment A which is to be fixed onto the remainder of the main bone B, by advancing the threaded portion 3 into the main bone.

The half-angle of conical shoulder convergence, i.e., with respect to the central axis of pin 1, is suitably in the range 30° to 60°, and is preferably about 45°.

Alternatively, and as shown in FIG. 3, a compression wire or pin may have a substantially radial shoulder 4' between its smooth shank 2 (diameter $D_1$), adapted for drill-chucked drive, and its reduced self-tapping threaded end 3 (of diameter $D_2$), in which case, a fixation as in FIG. 2 will be understood to use shoulder 4' for larger-area contact with the fragment A to retain a predetermined retaining force of fragment A against the remainder B of the same bone. FIG. 3 further serves to identify overall length $L_1$ and threaded length $L_2$, as well as to indicate at $\alpha$, the ground angle of convergence of the self-tapping distal end of threaded portion 3; the angle $\alpha$ is suitably about 45°.

To obtain an idea of the sizes involved, it is pointed out that a fixation pin 1, may for example, have a length of 100-mm, with the threaded portion 3 having a length of 15-mm, and the shank portion 2 a length of 85-mm. The diameter of the threaded portion can be 1.4 to 1.6-mm when, for example, the diameter of the shank portion 2 is 2-mm.

More specifically, and by way of example, a fixation pin 1 should be of such overall length ($L_1$) as to permit well-chucked engagement to the shank portion 2, with a generous allowance of exposed shank, for unobstructed viewing by the surgeon; this can be taken to mean at least a viewable 25-mm length of shank to the shoulder region 4, when chucked to a portable drill. And to provide the surgeon with a range of fixation pins sufficient for the wide variety of small-bone fractures encountered in practice, it is currently preferred to provide sets or kits of such pins, in three standardized shank diameters, namely 1.5-mm, 2.0-mm and 3-mm diameter respectively, and to provide all pins to the same overall length ($L_1$) of at least 100-mm and preferably 120-mm; however, larger-diameter pins, to at least 5-mm diameter, are presently contemplated. In general, it is considered suitable to provide the outer diameter $D_2$ of all threaded ends 3 at a 70 to 80 percent relationship to the shank diameter, and to provide progressively stepped increments of thread length ($L_2$) in a full assortment that is preferred for each shank diameter. Thus, for a small 1.5-mm diameter shank-size assortment, thread length ($L_2$) is selectable from a preferred group of eight pins, ranging in 2-mm increments from 7-mm to 21-mm, wherein all threads are of 1.2-mm diameter, all to serve for fixation of the smallest fragments in small bones. Thus also, for a large 3-mm diameter shank-size assortment, thread length ($L_2$) is selectable from another preferred group of eight pins, ranging in 5-mm increments from 20-mm to 55-mm, wherein all threads are of 2.2-mm diameter, all to serve for fixation of larger fragments in relatively large bones. The intermediate or 2-mm diameter shank assortment is currently preferred to serve intermediate situations, wherein thread length is in small (e.g., 2-mm) increments in a range 11-mm to 25-mm, and in larger (e.g., 5-mm) increments for greater threaded lengths, all with 1.6-mm thread diameter.

With the indicated orders of dimensional magnitude, and after a selected pin has been driven in a single operation to drill and thread itself to the point of full thread implantation, to fixate a bone fragment, the shank portion 2 can easily be cut off by suitable nippers so that protruding regions of the threaded portion or of the shank portion can easily be removed. With proper selection of thread length, there should be no distally protruding length of the threaded portion, and the shank-portion cut-off should be below skin level, but with sufficient proximal protrusion to permit chucked engagement, for later unthreading extraction purposes.

Depending upon the externally exposed shape or condition of a particular bone fragment to be secured to the remainder of the same bone, the invention is shown in FIG. 4 to permit optional employment of a washer 6, which, as in the case of all or any pins of the invention, is also preferably and suitably of stainless steel. In FIG. 5, diametric dimensions $D_1$ and $D_2$ identify the sizes and size relationships discussed above for the shank and threaded portions (2, 3) of the pin of FIG. 3, namely, with a radial shoulder 4' between shank 2 and the threaded end 3.

Washer 6 is flat and features a bore of diameter $D_3$ to clear the threads of portion 3 and a conical counterbore or chamfer at both ends of the bore. The outer diameter $D_4$ of the washer may suitably be 1.5 to 2.5 times the shank diameter $D_1$. The inner diameter of the chamfer is the bore diameter $D_3$, which is less than the shank diameter $D_1$; and the outer diameter $D_5$ of the shank diameter $D_1$; and the outer diameter $D_5$ of the chamfer exceeds the shank diameter $D_1$, to an extent which is at least at the radial clearance between the washer bore and the thread diameter $D_2$. In these circumstances, the driven fit of shoulder 4' to washer 6, with washer 6 compressing bone fragment A to bone remainder B, may be a perfectly centered engagement of the circular rim of shoulder 4' to the adjacent chamfer, as shown; and it is also possible for washer 6 to be slightly angled (i.e., tilted) in self-adaption to a local profile or other feature at washer contact with fragment A, in which case, shoulder 4' engagement to the adjacent chamfer of the washer will be at only slight departure from the circle-to-cone engagement for the perfectly centered situation. In any event, the slight tilting of washer 6 with respect to a normal to the central axis of the pin will in no sense impair a shank-driven washer compression of bone fragment A to bone remainder B.

In FIG. 5, the same washer 6, with like preferably 45-degree chamfers at opposite ends of its bore, is shown in combination with a pin as in FIGS. 1 and 2, namely, with a conical transition 4 between shank and threaded ends of the pin. The involved cone-to-cone engagement is self-centering, and washer is urged to assume an orientation perpendicular to the pin axis when shank 2 is driven to apply fragment-fixation compression over the area of the fracture X.

In FIG. 6, washer 6' has a distal face 7 that is concave, being suitably a circular or parabolic arc of revolution about the axis of the bone pin. The axial depth d of the concavity 7 may be about one-third of the axial extent of washer 6'. The small-bone fragment A is of course enlarged but is seen to present a concave shape for washer (6') engagement with the convex shape of the bone fragment, in close conformance with the concave depth and curvature of the distal face 7 of the washer. This is as it should be for the fracture X as shown in FIG. 6, wherein bone-engagement via distal face 7 provides an enlarged area of bone-fragment support and compression surrounding the region of threaded-portion (3) engagement to bone at A and at B.

It is realized, however, that not all bone fragments will present a convex shape that is so well accommodated by the distal face 7 that has been described. To best equip the orthopedic surgeon who must deal with whatever confronts him, the invention is to be understood as being available in kit form, wherein at least one and preferably several washers 6 are provided for each bone screw, pin, or wire 1, and wherein the several washers 6 differ as to axial depth d of the concavity 7. The surgeon has further opportunity to adapt the described washer 6 to particular circumstances of small bone fragment contour, in that the washer 6 may be bent as necessary by pliers or other tools which are standard equipment for the orthopedic surgeon. Thus, if need be, a washer 6', of preselected axial depth d of its otherwise spherical distal face 7 may be bent to distort the distal face 7 into a more complex curvature wherein the curvature is, for example, (i) of relatively short-focus parabolic nature in a first longitudinal section which includes the pin axis and (ii) of longer-focus parabolic nature in a second longitudinal section, taken 90 degrees from the first longitudinal plane.

A kit of the nature indicated preferably includes a set of small-bone pins or compression wires 1, wherein there is at least one pin or wire 1 of each of several shank (2) diameters, illustratively of 3-mm, 2-mm, and/or 1.5-mm diameter, with thread (3) diameters of 2.2-mm, 1.6-mm, and/or 1.2-mm, respectively, in ranges of incrementally stepped thread lengths, as noted above for each of the respective thread lengths. Such a kit would also include washers 6 (and/or 6') at least to fit the 3-mm and 2-mm shank sizes indicated, and with at least two different axial depths d for each of these shank sizes. In the case of the 3-mm shank size, washers 6 are suitably of 6-mm or 4-mm diameter $D_4$; nd in the case of the 2-mm or 1.5-mm shank size, washers 6 are suitably of 3-mm or 4-mm diameter $D_4$.

Each compression wire of the invention provides sufficient length of smooth-walled shank to enable chucked engagement to a standard portable drill, preferably of so-called "cordless" variety. Procedurally, each wire can be installed in a single driven self-drilling and tapping operation with entry into both the small bone fragment and the larger remainder of the same bone, from which the small fragment was broken. The wire is set, upon driven rotational entry into the bone, to the extent of shoulder compression of the fragment A to the anchored remainder B of the same bone. In the course of driving the pin through the fractured bone, reduction is maintained by pressure applied to the fragment; and the shoulder keeps the bone fragment from back-sliding when the shoulder reaches the cortex of the fragment. After wire-threading (pin-threading) purposes have been served, the shank portion is no longer necessary and can be readily severed from the installed remainder, using a conventional wire-snip tool, as closely offset as possible from the shoulder 4 (4') region, which is relied upon to retain the fixation of fragment A to remainder B, it being understood that sufficient shank exposure at small offset from bone should remain, for later chucking and implant-unthreading purposes.

FIGS. 7A to 9B provide illustration of a variety of uses of the invention, which in all cases not only simplifies and shortcuts the process and time required for fragment fixation, but also enables greatly enhanced and assured durability of the fixated product, i.e., with compression-wire implantation.

In FIG. 7A, two large compression-wire implants 10, 11, e.g., 3-mm wire size, are shown with shanks cut off after self-tapping thread advance to the point of shoulder-driven fragment engagements to other fragments A', A" and to the tibial remainder B, in the case of a tibial pilon fracture. And in FIG. 7B, a single compression-wire implant 12 of the same large wire size, is seen to be retaining a fragment A to bone remainder B in reduction of a medial malleolar fracture.

Figure 8A:
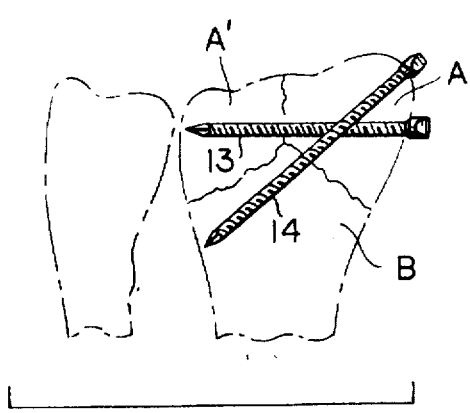
FIG. 8A is a diagram as in FIG. 7A, to show use of multiple compression wires, of medium-size wire, in the fixation of a distal-radius fracture.
Figure 8B:
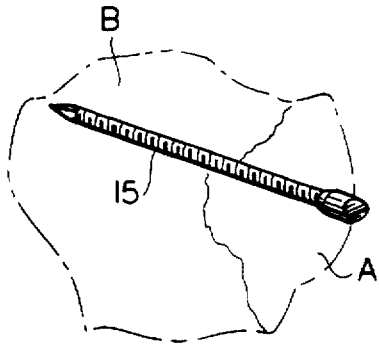
FIG. 8B is a diagram as in FIG. 7B, to show use of a single medium-size compression wire, in the fixation of a proximal radial fracture.

In FIG. 8A, first and second medium-size compression-wire implants 13, 14, e.g., 2-mm wire size, with shanks cut off after implantation, are shown retaining an outer fragment A to remainder bone B and to another fragment A+, for the case of an intra-articular distal radius fracture. And in FIG. 8B, a single compression-wire implant 15 of the same medium-size wire, is seen to be retaining a fragment A to remainder bone B in reduction of a proximal radius fracture.

Figure 9A:
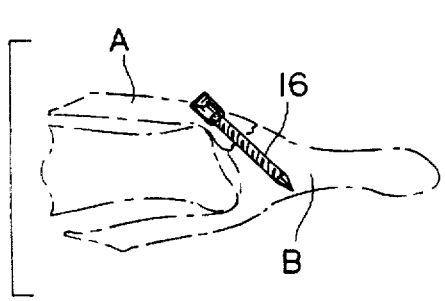
FIG. 9A is a similar diagram, to show use of a small-size compression-wire implant, in the fixation of a mallet-finger fracture.

In FIG. 9A, a single small and short compression-wire implant 16, e.g., 1.5-mm wire size, with shank cut off after implantation, is shown retaining a mallet finger A to remainder bone B. And in FIG. 9B, a single, relatively elongate compression wire 17 of small-wire size is shown fixing a fragment A to remainder bone B, in reduction of an intra-articular phalangeal fracture.

It is important to the invention that the threaded portion of the pin or compression wire shall be able to develop a self-drilling and self-tapping engagement in bone tissue, and particularly in the cancellous region which characterizes the respective ends of a given bone. Generally speaking, any bone consists of two types, with a continual gradation between the two types. Thus, cortical-bone structure exists between and merges integrally with cancellous-bone structure of bone ends. Cortical bone has a very defined structure centered around Haversian canals, which contain small blood vessels; lamellae or sheets of bone are arranged cylindrically, and the mineral structure of cortical bone is dense, so that self-tapping threaded entry and implantation in cortical bone presents no problem of securing implant anchorage.

On the other hand, cancellous bone exists under a thin (e.g., 1 to 2-mm thick) outer layer of cortical-tissue and has the appearance of a spongy or porous structure which consists of a network of rigid intersecting lamellae (or trabeculae) which appear to be randomly oriented but tend to be aligned in the direction of forces acting through the bone, either in compression or tension, and which are flat rather than cylindrical. The boundary or transition between cortical and cancellous bone consists of a gradual change in the spacing and orientation of these bone sheets; there is no clearly defined boundary. The lamellae of cancellous bone are usually arranged in a crisscross manner, which accounts for the visibly spongy or cellular appearance of the trabeculae. The trabeculae of cancellous-bone structure have walls that are dense and strong and are generally 0.1 to 0.5-mm thick; and the size of lacunae occupied by cells within the trabecular network ranges, with gradation, from 0.1-mm to about 3-mm, with sizes from 1 to 3-mm being common in the central region of cancellous bone.

It is important to note that the cutting tip and finely threaded nature of the described compression wires means that, in a single drilling advance of a compression wire along its intended path for implantation in cancellous bone, the thin outer cortex layer will first be drilled with accompanying small chips generated but not expelled from the path of self-drilling and self-tapping advance. Further small chips will be generated at each intercept of and passage through successive trabeculae, but none of the chips will be expelled or wasted. Photographic analysis reveals that as these chips are generated, the chips are locally impacted in the softer contents of successive lacunae along the cancellous-bone path that is generated by drilling and threading advance of the compression wire. The lacunae are thus filled and acquire enhanced density, and all implanted threads of the fully driven compression wire become engaged, thereby establishing a continuous base for enhanced anchorage in chip-impacted lacunae, as well as in trabeculae along the path of threaded advance.

The foregoing discussion of cancellous bone, as compared to cortical bone, will be seen to be particularly relevant to the illustrative bone-fragment circumstances of FIGS. 7 (A and B), 8 (A and B), and 9 (A and B), all of which involve fragments of cancellous bone, to be anchored to more cancellous bone.

Figure 9B:
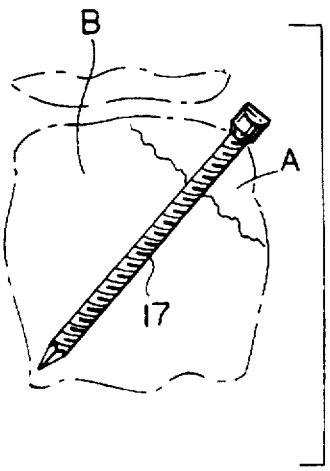
FIG. 9B is another diagram for use of a small-size compression-wire implant, in the fixation of an intra-articular phalangeal fracture.

The indicated preference for three sizes of compression wire used in the circumstances of FIGS. 7A to 9B will be seen not only to accommodate to the smallest bone size, such as the 1.5-mm wire size (with 1.2-mm diameter threaded portion) in FIGS. 9A and 9B, but also to develop maximum thread engagement to trabeculae of cancellous-bone having the smallest structure. Stated in other words, it is important that the helical advance of the threaded portion of a given compression wire that is selected for fixation of a fragment of small bones shall be so fine as to assure at least one and preferably several turns of thread engagement, for compression-wire threaded advance through each or most of the trabeculae along the path of threading advance; in view of the somewhat random orientation of trabecular walls and the variety of alignments of compression-wire implantation, thread advances will be predominantly with skewed incidence to trabecular walls, thereby increasing the likelihood of multiple-thread engagement to all trabecular walls. Thus, for the small 1.5-mm wire size (with 1.2-mm thread diameter), a fine-thread advance of 0.25-mm per turn is preferred for maximum assurance of thread anchorage to the honeycomb-like network of trabecular structure to be engaged. The larger above-noted compression-wire sizes are also preferred with fine-thread advances consistent with achieving secure anchorage in the cancellous structures that they are intended to implant. In the case of the intermediate 2-mm wire size (with 1.6-mm diameter threaded portion), the preferred threaded-portion advance per turn is 0.35-mm;

and in the case of the 3-mm wire size (with 2.2-mm diameter threaded portion), the preferred threaded-portion advance per turn is 0.45-mm.

The compression-wire configuration of FIGS. 10 and 11 (A and B) represents presently preferred relationships, generally as described in connection with FIGS. 3 to 6 but different in the following respects:

1. A frusto-conical transition zone 20 at which shank diameter $D_1$ reduces gradually to the outer diameter $D_2$ of the threaded portion 3, at an included angle $\beta$ in the range 25 to 35 degrees; and
2. A bone-cutting distal-tip end characterized by three angularly spaced ground truncations 22, 23 which converge to a distal point on the longitudinal axis of the wire.

In FIG. 11A, the threaded advance or pitch is denoted p, and will be understood to be preferably consistent with quantities expressed above for the three rod sizes presently contemplated for compression wires of the invention. In all cases, preference is indicated for confronting adjacent faces of successive turns of the threaded portion 3 to be at substantially the same angle $\gamma$ of 60 degrees and for the thread depth A to be in the range of 12 to 14 percent of the thread diameter $D_2$.

Although the discussion thus far has addressed problems of bone-fragment fixation to remaining structure of the same bone, it is to be understood that compression-wire constructions as presently disclosed are eminently suited to other fixation tasks. For example, as illustrated in FIG. 12, two implanted upper compression wires 25, 26 and two implanted lower compression wires 27, 28 retain a lateral buttress plate which supports a cortico-cancellous graft in a patient's tibia.

What is claimed is:

1. An elongate compression wire for fixating a fragment of a fractured bone to remainder structure of the same fractured bone in an osteosynthesis procedure, said wire having a shoulder between proximal and distal ends, said wire having a central axis and comprising a smooth-walled cylindrical shank portion extending from said shoulder to said proximal end and adapted for selective chuck engagement to a rotary power tool, said shank portion having a diameter in the range 1.5 to 3.0-mm and having a self-tapping threaded portion of lesser diameter than that of said shank, and said threaded portion having an advance per turn in the range 0.2 to 0.5-mm, wherein said threaded portion extends distally of said shoulder, whereby said wire may be power-driven for self-tapping threading advance through the bone fragment and into implantation in remainder bone structure to an extent of shoulder contact with cortex tissue of the bone fragment and bone-fragment retention against remainder bone structure.

2. A compression wire according to claim 1, wherein the diameter of said threaded portion is in the range of approximately 70 to 80 percent of the diameter of said shank portion.

3. A compression wire according to claim 1, wherein said shoulder is in substantially a radial plane normal to said axis.

4. A compression wire according to claim 1, wherein said shoulder is a frusto-conical reduction from said shank portion to said threaded portion.

5. A compression wire according to claim 4, in which said frusto-conical reduction has a half angle of convergence of about 30 degrees.

6. A compression wire according to claim 1, in which the wire is of a material that may be cut by a suitable nipper tool after implantation of said threaded portion.

7. A compression wire according to claim 6, in which said material is stainless steel.

8. A compression wire according to claim 1, in which said threaded portion has a cutting distal-tip end which is characterized by at least three angularly spaced ground surfaces which converge distally from distal threads of said threaded portion.

9. A compression wire according to claim 8, in which said angularly spaced surfaces are flat, adjacent flat surfaces intersecting to define bone-cutting edges which converge to a distal point on said central axis.

10. A compression wire according to claim 9, in which the number of said flat surfaces is three.

11. A compression wire according to claim 9, in which each of said surfaces converges with respect to said central axis at an angle in the range 12° to 18°.

12. A compression wire according to claim 9, in which each of said surfaces converges with respect to said central axis at an angle in the range 15° to 16°.

13. An elongate compression wire for fixating a fragment of a fractured bone to remainder structure of the same fractured bone or for fixating a bone graft or supporting plate to existing bone structure, said wire having a shoulder between proximal and distal ends, said wire having a central axis and comprising a smooth-walled cylindrical shank portion extending from said shoulder to said proximal end and adapted for selectively chucked engagement to a rotary power tool, said shank portion having a diameter in the range 1.5 to 3.0-mm and having a self-tapping threaded portion of a diameter in the range 1.2 to 2.2-mm, wherein the threaded portion extends distally from said shoulder and has a bone-cutting distal-tip end, and wherein the threaded portion has an advance per turn that is about one fifth of the thread diameter.

14. A compression wire according to claim 13, in which the thread diameter is about 1.2-mm, and the advance per turn is about 0.25-mm.

15. A compression wire according to claim 13, in which the thread diameter is about 1.6-mm, and the advance per turn is about 0.35-mm.

16. A compression wire according to claim 13, in which the thread diameter is about 2.2-mm, and the advance per turn is about 0.45-mm.

17. A kit comprising an elongate compression wire for fixating a fragment of a fractured bone to remainder structure of the same fractured bone or for fixating a bone graft or supporting plate to existing bone structure, said wire having a shoulder between proximal and distal ends, said wire having a central axis and comprising a smooth-walled cylindrical shank portion extending from said shoulder to said proximal end and adapted for selectively chucked engagement to a rotary power tool, said shank portion having a diameter in the range 1.5 to 3.0-mm and having a self-tapping threaded portion of a diameter in the range 1.2 to 2.2-mm wherein the threaded portion extends distally from said shoulder and has a bone-cutting distal-tip end, and wherein the threaded portion has an advance per turn that is about one fifth of the thread diameter; and a flat washer having a bore of diameter which exceeds the diameter of the threaded portion and which is less than the diameter of the shank portion, said washer having like chamfers at the respective ends of the bore, and the washer having an outer diameter which exceeds the diameter of the shank portion.

18. A kit according to claim 17, in which the shoulder of said compression wire is a frusto-conical transition from the smooth shank diameter to the diameter of the threaded portion, said frusto-conical transition having a first slope with respect to the central axis, and each of the chamfers having a second slope with respect to the washer-bore axis, said first slope being at a lesser angle than said second slope.

19. A kit according to claim 18, in which said first slope is in the range of 12 to 18 degrees, and in which said second slope is in the range of 40 to 50 degrees.

20. A kit according to claim 17, in which said compression wire is one of a plurality of compression wires of equal overall length, and in which the longitudinal position of said shoulder of one of said wires is different from the longitudinal position of said shoulder of another of said wires, whereby the longitudinal extent of the threaded portion of said one wire is different from the longitudinal extent of the threaded portion of said other wire.

21. A kit according to claim 17, in which said compression wire is one of a plurality of compression wires of equal overall length, and in which the longitudinal extent of the threaded portions of different compression wires of said plurality differ by successive integer multiples of a single increment of length.

22. A kit according to claim 21, in which the diameter of said threaded portion is in the range 1.2 to 1.6-mm, and in which the single increment of length is 2-mm.

23. A kit according to claim 21, in which the diameter of said threaded portion is in the range of 2.0 to 2.5-mm, and in which the single increment of length is 5-mm.

24. An elongate compression wire for fixating a fragment of a fractured bone to remainder structure of the same fractured bone in an osteosynthesis procedure, said wire having a shoulder between proximal and distal ends, said wire having a central axis and comprising a smooth-walled cylindrical shank portion extending from said shoulder to said proximal end and adapted for selective chuck engagement to a rotary power tool, said wire having a self-tapping threaded portion of lesser diameter than that of said shank, wherein said threaded portion extends distally of said shoulder and is characterized by a thread advance per turn in the range 0.2 to 0.5-mm, whereby said wire may be power-driven for self-tapping threading advance through the bone fragment and into implantation in remainder bone structure to an extent of shoulder contact with cortex tissue of the bone fragment and bone-fragment retention against remainder bone structure.

25. A compression wire according to claim 24, wherein the diameter of said threaded portion is in the range of approximately 70 to 80 percent of the diameter of said Shank portion.

26. A compression wire according to claim 24, wherein said shoulder is in substantially a radial plane normal to said axis.

27. A compression wire according to claim 24, wherein said shoulder is a frusto-conical reduction from said shank portion to said threaded portion.

28. A compression wire according to claim 27, in which said frusto-conical reduction has a half angle of convergence of about 30 degrees.

29. A compression wire according to claim 24, in which the wire is of a material that may be cut by a suitable nipper tool after implantation of said threaded portion.

30. A compression wire according to claim 29, in which said material is stainless steel.

31. A compression wire according to claim 24, in which said threaded portion has a cutting distal-tip end which is characterized by at least three angularly spaced ground surfaces which converge distally from distal threads of said threaded portion.

32. A compression wire according to claim 31, in which said angularly spaced surfaces are flat, adjacent flat surfaces intersecting to define bone-cutting edges which converge to a distal point on said central axis.

33. A compression wire according to claim 32, in which the number of said flat surfaces is three.

34. A compression wire according to claim 32, in which each of said surfaces converges with respect to said central axis at an angle in the range 12° to 18°.

35. A compression wire according to claim 31, in which each of said surfaces converges with respect to said central axis at an angle in the range 15° to 16°.

* * * * *

UNITED STATES PATENT AND TRADEMARK OFFICE
CERTIFICATE OF CORRECTION

PATENT NO. : 5,709,687
DATED : January 20, 1998
INVENTOR(S) : Dietmar PENNIG

It is certified that error appears in the above-indentified patent and that said Letters Patent is hereby corrected as shown below:

Column 6, line 35;   after "fragment" delete "A+" and insert therefor --A'--

Column 8, line 23;   after "thread depth" delete "A" and insert therefor -- Δ--

Claim 25, line 3;   delete "Shank" and insert therefor --shank--

Signed and Sealed this

Fifth Day of May, 1998

Attest:

BRUCE LEHMAN

Attesting Officer    Commissioner of Patents and Trademarks